United States Patent
Lindquist

(10) Patent No.: US 6,368,109 B2
(45) Date of Patent: *Apr. 9, 2002

(54) KITS FOR USE IN ACCELERATING DENTAL TREATMENTS

(75) Inventor: Sherrill F. Lindquist, Dublin, OH (US)

(73) Assignee: Ultradent Products, Inc., South Jordan, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/847,092

(22) Filed: May 1, 2001

Related U.S. Application Data

(63) Continuation-in-part of application No. 09/565,752, filed on May 8, 2000.

(51) Int. Cl.[7] .............................................. A61C 5/00
(52) U.S. Cl. ........................................ 433/215; 433/37
(58) Field of Search ............................ 433/6, 32, 34, 433/48, 74, 213, 214, 215, 229

(56) References Cited

U.S. PATENT DOCUMENTS

| | | | |
|---|---|---|---|
| 1,084,017 A | 1/1914 | Lautenburg | |
| 2,110,860 A | 3/1938 | Grempler | 32/17 |
| 2,257,329 A | * 9/1941 | Britt | |
| 3,207,161 A | 9/1965 | Dietz | 128/404 |
| 3,216,139 A | 11/1965 | Dietz | 128/172.1 |
| 4,445,854 A | * 5/1984 | Bekey et al. | 433/37 |
| 4,959,013 A | 9/1990 | Reynolds | 433/35 |
| 4,983,381 A | 1/1991 | Torres Zaragoza | 424/53 |
| 5,177,120 A | 1/1993 | Hare et al. | 523/109 |
| 5,211,559 A | 5/1993 | Hart et al. | 433/80 |
| 5,316,473 A | * 5/1994 | Hare | 433/229 |
| 5,421,727 A | 6/1995 | Stevens et al. | 433/224 |
| 5,487,662 A | * 1/1996 | Kipke et al. | 433/229 |
| 5,494,441 A | 2/1996 | Nicholson | 433/215 |
| 5,698,610 A | 12/1997 | Futami et al. | 523/109 |
| 6,102,705 A | * 8/2000 | Darnell | 433/216 |

* cited by examiner

Primary Examiner—Nicholas D. Lucchesi
(74) Attorney, Agent, or Firm—Workman, Nydegger, Seeley

(57) ABSTRACT

Apparatus, kits and methods for providing accelerated treatment of a patient's teeth. The apparatus, kits and methods involve the use of a dental impression tray that includes a patient dentition impression formed from a dental impression material such as an alginate. The impression tray advantageously includes a heating element for heating and maintaining the formed patient dentition impression at a temperature greater than about 105 degrees F. The heated dental trays may be used to accelerate the activity of dental bleaching agents (e.g., peroxides), desensitizing agents (e.g., potassium nitrate), remineralizing agents (e.g., fluoride salts), and the like. A dental office procedure for treating teeth involves the basic steps of: (1) coating a specially-prepared patient dentition impression with a dental composition such as a bleaching, desensitizing or remineralizing composition; (2) placing the coated patient dentition impression into the patient's mouth; (3) heating the patient dentition impression and dental composition to a temperature of at least about 105° F.; and (4) retaining the patient dentition impression in position for period of time in a range of about 1 minute to about 60 minutes. The procedure can be adapted to microwave heating, electrical resistance heating, or hot fluid heating of the patient dentition impression.

24 Claims, 9 Drawing Sheets

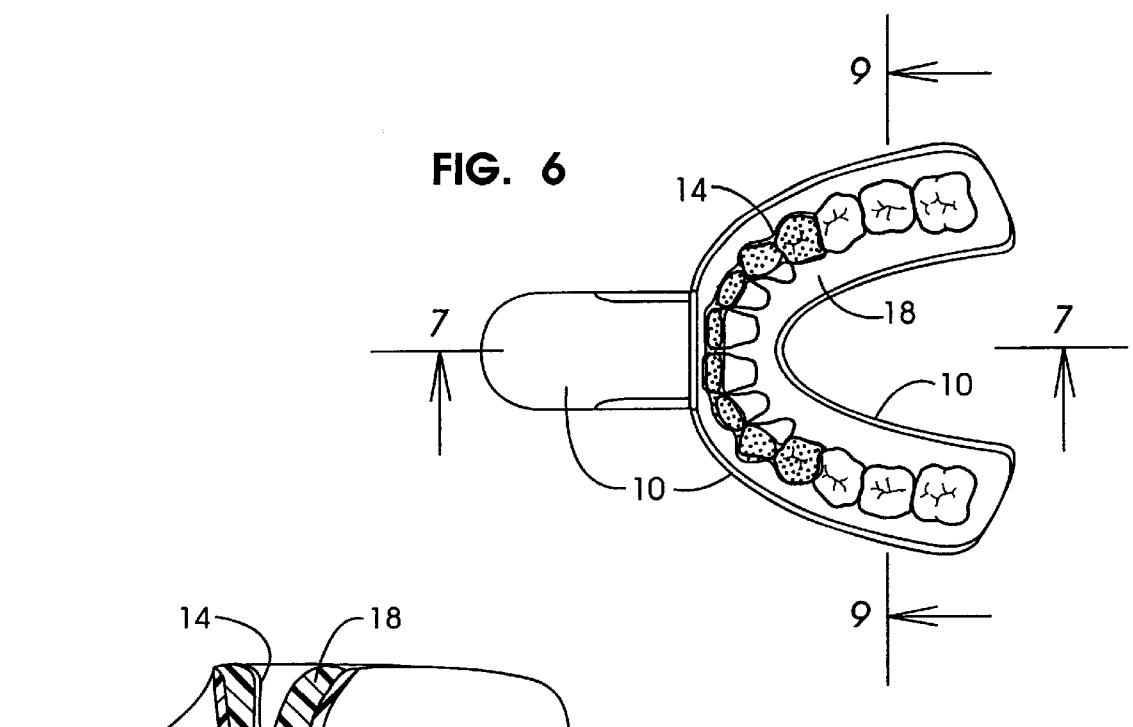
FIG. 6
FIG. 7
FIG. 8
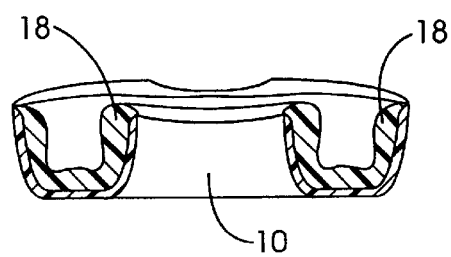
FIG. 9
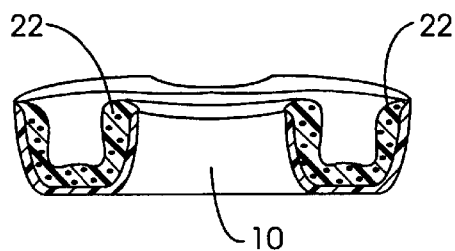
FIG. 10

KITS FOR USE IN ACCELERATING DENTAL TREATMENTS

RELATED APPLICATION

This application is a continuation-in-part of copending U.S. application Ser. No. 09/565,752, filed May 8, 2000. For purposes of disclosure, the foregoing applications are incorporated herein by specific reference.

BACKGROUND OF THE INVENTION

1. Field of the Invention

This invention is in the field of apparatus and methods for use in accelerating the activity of dental bleaching compositions. More particularly, the invention is in the field of apparatus and methods for accelerating the activity of e.g., dental bleaching, desensitizing and remineralizing compositions by means of a heated dental impression material.

2. Review of the Relevant Technology

In the last decade there has been a proliferation of compositions and methods for bleaching teeth. Compositions for both in-office or at-home use typically include a peroxide bleaching agent, such as carbamide peroxide, hydrogen peroxide or sodium perborate. Carbamide peroxide is a complex of urea and hydrogen peroxide. Sodium perborate is a complex of sodium borate and hydrogen peroxide. On the other hand, hydrogen peroxide by itself only exists in aqueous form and is generally unstable except at relatively low pH.

When formulating an appropriate bleaching composition there is inherently a tradeoff between stability and reactivity. It is desirable for a bleaching composition to remain stable between the time when it is manufactured and when it is used to bleach a person's teeth. However, once placed on a person's teeth it is desirable for the composition to quickly break down and release active oxygen radicals capable of bleaching teeth. In general, compositions that are sufficiently stable so as to have good shelf life tend to bleach teeth slowly over time, typically over a period of weeks with daily regimens of from one to eight hours. On the other hand, bleaching compositions that are capable of bleaching teeth in shorter periods of time generally do not have a long shelf life and are typically prepared just prior to application to a person's teeth.

There are at least two known ways of triggering accelerated decomposition of active oxygen radicals from peroxide-containing bleaching compositions. One way is through the use of chemicals or catalysts that are known to destabilize peroxides. Such agents are typically mixed in with the peroxide bleaching agent just prior to application to the person's teeth.

Another way to accelerate the bleaching activity of peroxide-based bleaching compositions is through the application of heat. Examples of apparatus used to generate heat include conventional dental curing lamps used to cure composites and lasers. A draw-back that is common to both curing lamps and lasers is that it is typically not possible to simultaneously heat all of a patient's teeth, thus increasing the time it takes to complete the bleaching process as well as leading to the possibility of unequal application of heat to the various teeth. Another drawback to the use of a curing lamp, particularly one that is able to focus light or heat energy to an area that is greater than the size of the labial surface of a tooth to be bleached, is that the curing lamp tends to be indiscriminate as to whether it heats the tooth or surrounding gingival tissue, thus potentially causing discomfort to the patient. Accordingly, it is typically necessary to protect the patient's gingival tissue through the use of a protective rubber dam coating material.

In the case of at-home bleaching regimens, a customized patient bleaching tray or mouth guard is typically formed using a multi-step procedure. This procedure typically includes the steps of (1) making conventional alginate impressions of the patient's maxillary and/or mandibular teeth, (2) preparing stone cast models of the patient's upper and lower teeth from the alginate impressions using plaster of paris, followed by trimming away of the excess plaster, (3) blocking out on the trimmed cast stone models, using a conventional light-cured or light-activated, acrylic-based resin laboratory block-out gel, those tooth areas to be whitened so as to form reservoirs in the resulting tray, (4) vacuum forming a 5-inch by 5-inch sheet of 0.040-inch to 0.080-inch thickness clear plastic resin mouth guard material over each stone cast model, (5) removing the tray from the model, and (6) suitably trimmiing the tray so that it doesn't overlap the gingival margin. In some cases the tray is "scalloped" by trimming up and around the dental papilla. The dental tray is then ready for delivery to the patient as part of the home-use whitening kit. Home-use bleaching regimens employing the custom dental tray and whitening composition (e.g., a carbamide peroxide gel) typically involves a series of 1 to 8 hour bleaching treatments repeated daily over a period of about 2 to 6 weeks depending upon the degree or severity of dentition staining.

In view of the foregoing, there has been a long felt need in the art to provide apparatus and methods for use in accelerating the bleaching activity of conventional bleaching compositions in a manner that is both more comfortable from the point of view of the patient and more economical in terms of cost and time. It would be particularly useful of such apparatus were disposable, that is, of sufficiently low cost and simplicity of design so that it could be used for a single patient and then disposed of.

It would be a further advancement in the art if the foregoing apparatus and methods could be used to accelerate the activity of other dental compositions, e.g., desensitizing and/or remineralizing compounds that include potassium nitrate and/or fluoride salts.

Such apparatus and methods for increasing the activity of bleaching, desensitizing and remineralizing or other dental compositions are disclosed and claimed herein.

SUMMARY AND OBJECTS OF THE INVENTION

The present invention relates to apparatus and methods used to accelerate the activity of dental compositions by means of the application of heat. In particular, the invention relates to apparatus and methods for treating teeth that involve conventional or specially adapted dental impression trays in conjunction with a heated impression material. The use of impression material provides the dentist with the ability to manufacture what is, in essence, a customized tray that can be immediately used to treat a patient's teeth using a variety of dental compositions, (e.g., dental bleaching, desensitizing, or remineralizing compositions). The formed impression material can be heated by, e.g., microwave energy, resistive heating devices, or a heated fluid in order to accelerate the rate at which the dental composition is able to carry out its intended treatment of a patient's teeth.

The apparatus according to the present invention may advantageously be sold or provided to a dentist in the form of one or more kits that include at least a portion of the means necessary to form and then heat a dentition impression of the patient's teeth, followed by treatment of a patient's teeth using an appropriate dental composition. Such kits will preferably include, at a minimum, a dental impression tray capable of receiving sufficient impression material so as to make an impression of at least a portion of the patient's teeth, means for heating the impression during the treatment process, and one or more dental compositions, such as compositions that include at least one of a dental bleaching agent (e.g., a peroxide bleaching agent), a desensitizing agent (e.g., a potassium salt such as potassium nitrate), or a remineralizing agent (e.g., a fluoride salt such as sodium fluoride). The kits may optionally include an impression material, such as a standard alginate impression material known in the art. Nevertheless, because most dentists already have standard impression materials on site for other purposes, it is typically not necessary for the kits to include such impression materials.

A preferred embodiment of utilizing the apparatus disclosed herein to carry out accelerated treatment of a patient's teeth includes the following steps: (1) filling at least a portion of a dental impression tray with an unset dental impression material; (2) placing the filled dental impression tray into the patient's mouth in order to take an impression of at least a portion of the patient's teeth; (3) maintaining the impression tray in place for a sufficient length of time for the dental impression material to at least partially cure to thereby form a patient dentition impression; (4) removing the dental impression tray and included formed s patient dentition impression from the patient's mouth; (5) placing an appropriate quantity of a dental composition within the formed patient dentition impression; (6) introducing the dental impression tray and included formed patient dentition impression with the dental composition into the patient's mouth so as to at least approximately register the patient's teeth and the corresponding formed patient dentition impression; (7) heating and/or maintaining the temperature of the formed patient dentition impression at a temperature of at least about 105° F.; and (8) removing the dental impression try and included dentition impression from the patient's mouth and thoroughly rinsing the patient's mouth prior to release of the patient.

In a preferred embodiment, the formed patient dentition impression will be heated to and maintained at the desired temperature by means of an electrical resistance heating element located within, or otherwise associated with, the dental impression tray. The dentition impression may alternatively be heated by means of microwave energy or by the use of a heated fluid. The temperature of the dentition impression is preferably maintained in a range of about 110° F. to about 150° F., more preferably in a range of about 120° F. to about 140° F.

In the case where an electrical resistance heating element is used, the dental impression tray will be electronically connected to a power supply, such as a DC power supply that supplies a desired amount of power. In a preferred embodiment, the patient may be given a control device that interacts with the power supply so as to heat and maintain the dentition impression at an elevated, yet comfortable, temperature so as to optimize patient comfort and dental composition activity. In order to further maximize patient comfort, it may be advantageous to trim away a portion of the patient dentition impression that would otherwise contact or overlap the patient's gingival tissue. In this way the heat can be concentrated or focused on the teeth and kept away from the much more sensitive gingival tissue surrounding the teeth.

The treatment times according to the present invention typically range of about 1 minute to about 60 minutes, more preferably in a range of about 5 minutes to about 30 minutes, depending on the dental composition being used, as well as the time necessary for carrying out a desired treatment. Where it has heretofore been known that heat is able to destabilize peroxide-based dental bleaching agents so as to accelerate the liberation of oxygen radicals used in bleaching teeth, it has heretofore not been known that heat can also accelerate the beneficial effects of other dental agents, such as desensitizing agents based on potassium nitrate or remineralizing agents based on fluoride salts. This is a surprising result since neither potassium nitrate nor fluoride salts decompose when heated to the temperatures described herein.

Accordingly, it is an object of the invention to provide apparatus and methods for use in accelerating the bleaching activity of conventional bleaching compositions in a manner that is both more comfortable from the point of view of the patient and economical in terms of cost and time.

It is a further object to provide apparatus that is disposable and that is of sufficiently low cost and simplicity of design so that it can be used for a single patient and then disposed of.

It is a further object of the invention to provide apparatus and methods that can be used to accelerate the activity of other dental compositions, such as desensitizing and/or remineralizing compounds that include potassium nitrate and/or fluoride salt.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings in which:

FIG. 6 is a plan view of the completed dental impression prior to wax overlay removal;

FIG. 7 is a cross-section view taken at line 7—7 of FIG. 6;

FIG. 8 is a cross-section view similar to FIG. 7 but after accomplishing wax overlay removal;

FIG. 9 is a cross-section view taken at line 9—9 of FIG. 6;

FIG. 10 is a cross-section view taken at line 9—9 of FIG. 8 but with an alternative dental impression material having a particulate filler dispersed therein;

DETAILED DESCRIPTION OF THE PREFERRED EMBODIMENTS

I. Introduction.

The present invention encompasses apparatus and methods for accelerated treatment of a patient's teeth, typically in an in-office procedure, utilizing a conventional or specially adapted dental impression tray in conjunction with a heated dental impression material. Examples of dental compositions that have been found to provide accelerated treatment when heated include bleaching, desensitization and remineralizing compositions. The impression material may be heated, e.g., by means of microwave energy, a resistive heating device, or a heated fluid so as to accelerate the rate at which the dental composition acts on the patient's teeth. Other optional steps may be performed, as desired.

The use of an impression material to make what is in essence a customized dental tray into which an appropriate dental composition can be loaded eliminates the time-consuming practice of manufacturing a customized dental tray. Moreover, the heated impression materials of the present invention are far less expensive than expensive lasers, or even relatively inexpensive curing lamps, but provide similar or even superior results. Because dental impression trays and impression materials are so inexpensive, they may be used once and then discarded.

II. Apparatus for Forming and Heating a Patient Dentition Impression.

The basic component of the apparatus and systems according to the invention is the dental impressing tray. One of the purposes of the dental impression tray is receive and retain a dental impression material during the formation of a patient dentition impression and also during subsequent treatment of the patient's teeth. The impression tray will advantageously include means for heating the formed patient dentition impression during the treatment process. Nevertheless, virtually any dental impression tray, both conventional or specialized, may be used within the scope of the present invention, in combination with an impression material, to form a dentition impression of a patient's teeth to be treated.

Examples of suitable dental trays that include means for heating a formed dentition impression are illustrated more particularly in FIGS. 13–21. More preferred are dental inpression trays that incorporate, or otherwise have associated therewith, a resistive heating element, such as the trays illustrated in FIGS. 13–14 and 17–21, which shall be discussed first.

Figure 13:
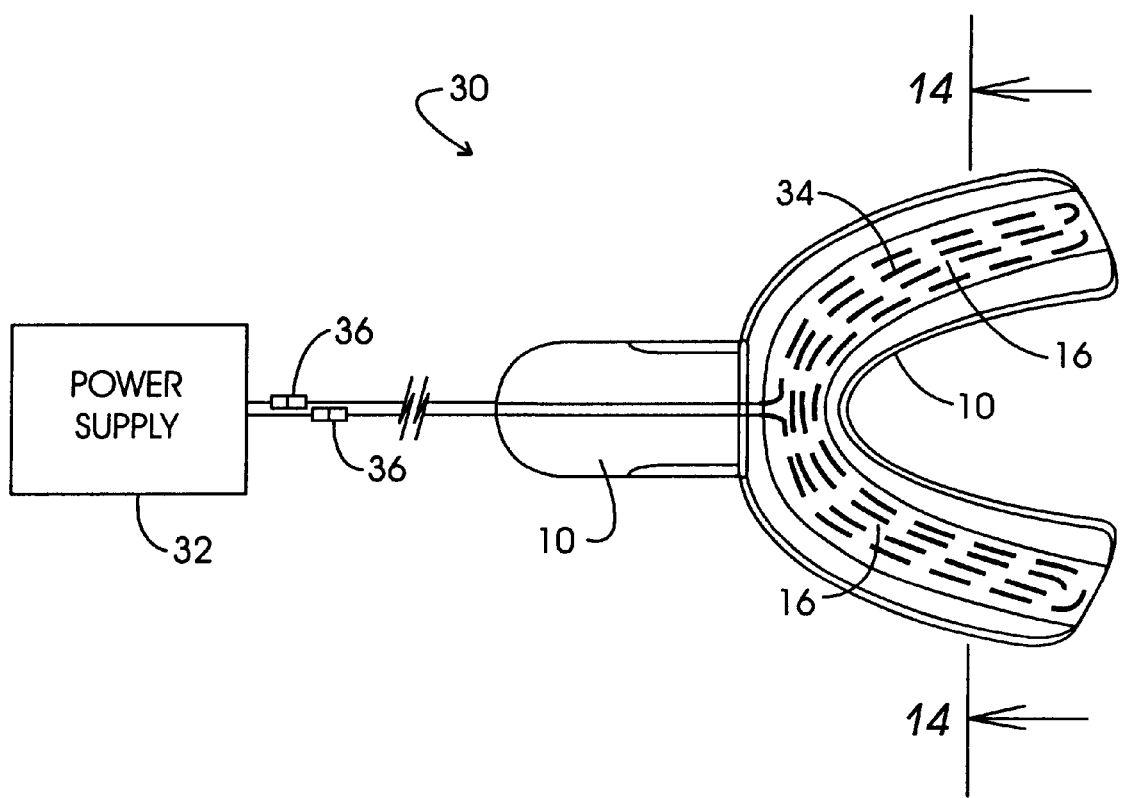
FIG. 13 schematically depicts an alternate embodiment of a dental impression material and impression tray in which resistive heat is employed to heat and maintain the proper temperature of the set dental impression material.
Figure 14:
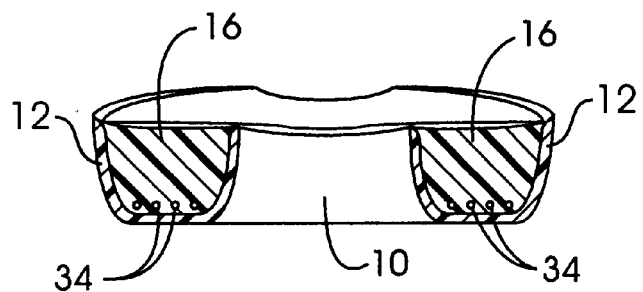
FIG. 14 is a cross-section view taken at line 14—14 of FIG. 13.

FIGS. 13 and 14 illustrate a dental impression tray 10 according to the present invention that includes a resistive heating element or wire. Impression tray 10 includes one or more heating wires 34 that are looped around within an interior cavity 12 of the tray 10 prior to filling tray cavity 12 with an unset or uncured dental impression material 16. During use, the one or more heating wires 34 are connected to a power supply 32. Together, the impression tray 10 and power supply 32 form a system 30 that is capable of heating the impression material 16 disposed within the interior trough of the tray 10. Because the impression tray 10 is advantageously disposable, or at least in order to separately store the tray 10 and power supply 32, the one or more heating wires 34 are advantageously coupled to the power supply 30 by means of conventional or specialized electrical connectors 36.

Although FIG. 14 depicts an arrangement wherein the heating wires 34 are embedded within the impression material 16, any arrangement whereby impression tray 10 is able to heat and maintain the impression material 16 within a desired temperature range is within the scope of the invention. In an experimental embodiment of apparatus 30, approximately 40 to 50 inches of No. 24 insulated audio speaker wire were used as resistance heating wire 34. Power supply 32 comprised a conventional 120/30 volt alternating current step-down transformer with a 2.5 ampere output current, an alternating current-to-direct current rectifier, an electronic intermittent switch having 30–40 second on times alternated with 30–40 second off times, and a system on-off timer switch mechanism The power supply timer functioned to activate power supply 32 for periods of time in a range of from 1 to 15 minutes.

Figure 17:
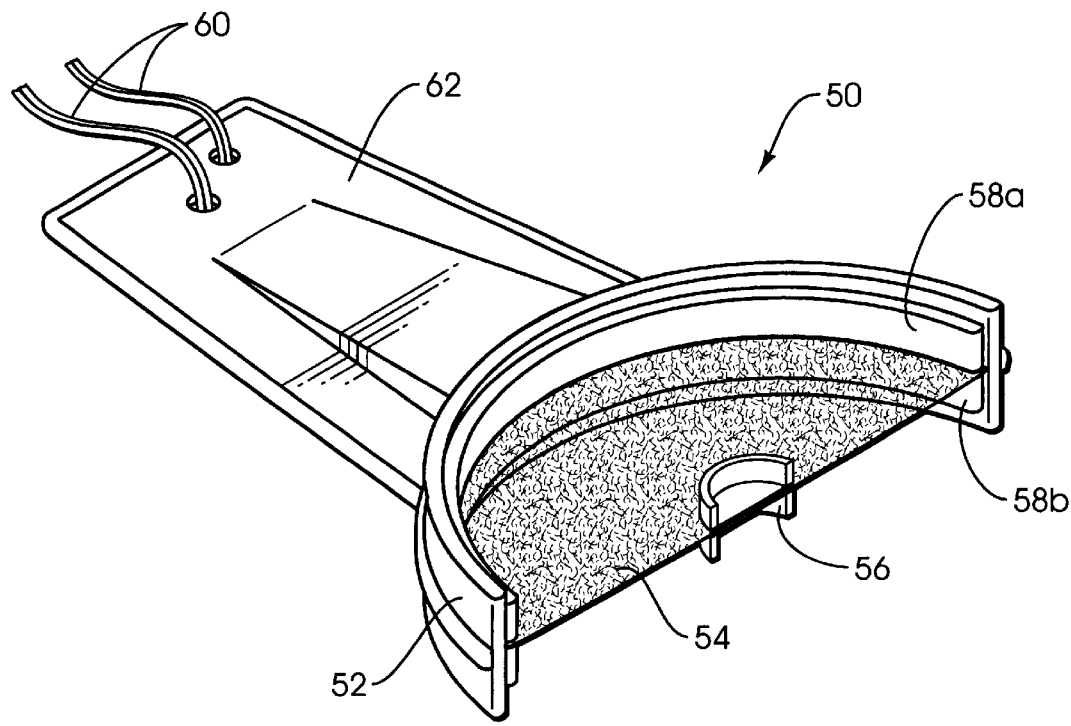
FIG. 17 is a perspective view of an alternative dental impression tray equipped with resistive heating elements.
Figure 18:
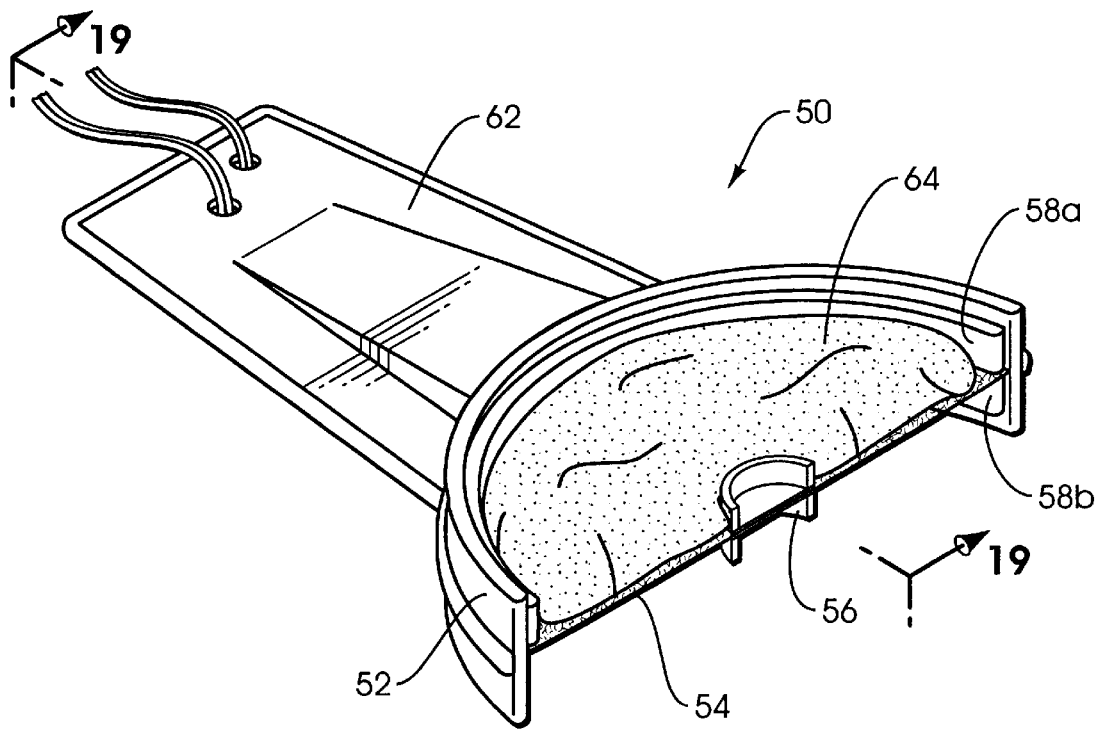
FIG. 18 is a perspective view of the dental impression tray of FIG. 17 into which a dental impression material has been placed into the upper half of the impression tray.
Figure 19:
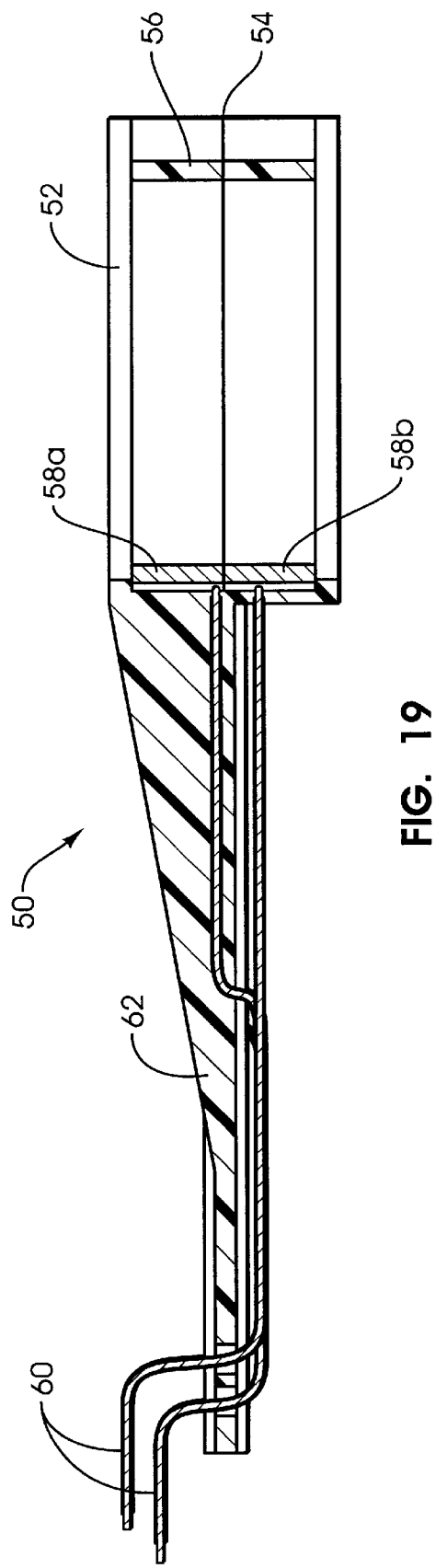
FIG. 19 is a cross-section view taken at line 19—19 of FIG. 18.

FIGS. 17–21 depicts an alternative dental impression tray 50 configured so as to be able to treat the upper and lower teeth of a patient of the same time. As shown in FIG. 17, dental impression tray 50 includes a generally arcuate structure 52, which defines an interior region for receipt of a dental impression material 64 (FIG. 18). Arcuate structure 52 is attached to a handle 62, which serves the dual purpose of facilitating gripping by the dental practitioner as well as providing a protective housing for wires 60 used to supply an electric current used to heat a formed dentition impression of the patient's teeth (not shown) within dental impression tray 50.

Tray 50 further includes a substantially planar divider or barrier 54, which provides opposing surfaces for placement of an impression material 64 on either side of divider 54. Divider 54 may comprise any appropriate material, examples of which include a solid metal or plastic sheet, or a wire or nylon fabric or mesh. A generally curved wall 56 assists in retaining the alginate or other impression material within the space between arcuate structure 52 and wall 56. FIG. 17 further depicts a pair of heating elements 58a and 58b disposed on an interior surface of arcuate structure 52, which are used to heat an impression material.

FIG. 18 depicts tray 50 into which an unset impression material 64 has been placed within the space defined by wall 56 and arcuate structure 52 on an upper surface of divider 54. In the case where it will be desired to bleach both the upper and lower teeth, a layer of impression material 64 may also be placed on the underside of divider 54. The use of a mesh or other porous material as the divider 54 promotes adhesion of the impression material 64 onto the surface of the divider 54, even on the underside. Of course, glue or other adhesion aids may be used as desired to retain the impression material 64 within the tray 50.

It will be appreciated that a person's gums or gingiva are typically more sensitive to heat than teeth. Accordingly, it may be desirable to trim back a portion of the cured impression material of the formed patient dentition impression in the area of the gingival interface. In this way the cured impression material advantageously touches or is adjacent to only the patient's teeth being treated rather than the more sensitive gingival tissue.

In order to heat the formed patient dentition during treatment, heating elements 58a and 58b heat up as an electrical current is passed therethrough. As more particularly shown in FIG. 19, wires 60 deliver an appropriate electrical current to heating elements 58a and 58b. In the case where the heating elements 58a and 58b are relied on to generate heat, they should comprise an appropriate high resistance metal or other poorly conductive material capable of generating heat when a current is passed therethrough.

In the alternative, heating elements 58a and 58b may passively act as heat sinks that assist in distributing heat generated by adjacent heating element wires in contact with elements 58a and 58b. In this way, elements 58a and 58b may not themselves generate heat but will act to better disperse heat over a wider area compared to heating element wires in contact with heating elements 58a and 58b. In such a case, the heating elements 58a and 58b may advantageously comprise a metal or other material that readily conducts heat, such as aluminum.

Figure 20:
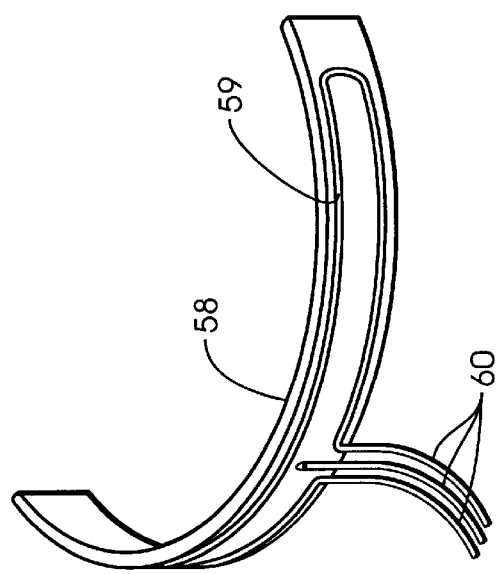
FIG. 20 is a perspective view of a heating element used in a dental impression tray according to the invention.

As more fully depicted in FIG. 20, heating element 58 includes a channel 59 into which one or more electrical wires 60 are placed so as to deliver an appropriate current to the heating element 58 in order to cause heating element 58 to generate heat. In the alternative, the one or more wires 60 may include a length of a heating wire, such as a Ni—Cad wire, disposed within channel 59. In this embodiment, the Ni—Cad wire, rather than the metallic heating element 58, will be primarily responsible for generating the heat used to heat up the patient dentition impression (not shown) formed from the impression material 64 in order to accelerate activity of the dental agent. In this case, metallic heating element 58 will act primarily as a heat sink used to transfer heat energy from the Ni—Cad wire to the impression material 64.

Figure 21:
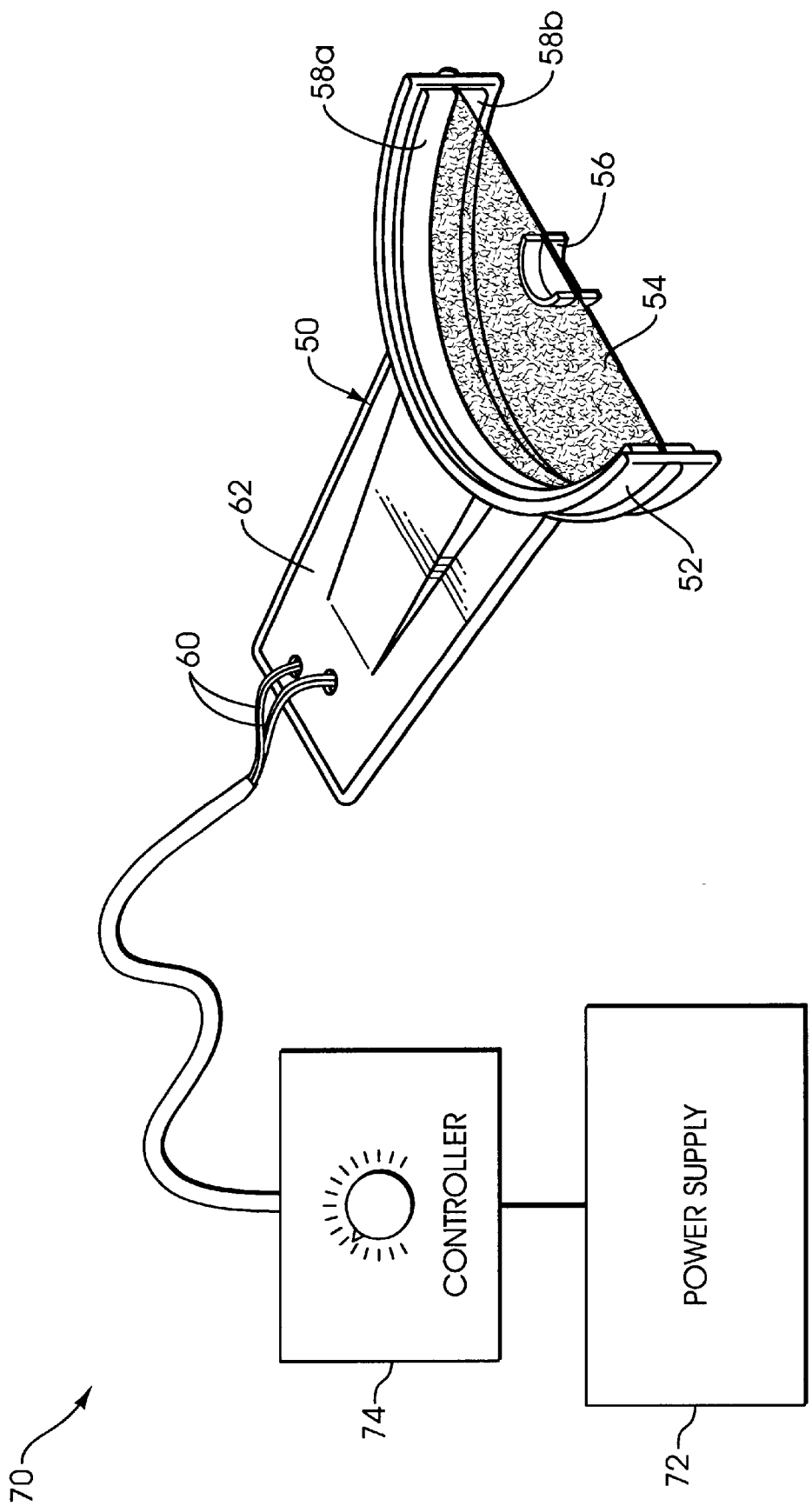
FIG. 21 schematically depicts an integrated system employing the impression tray of FIG. 17 together with a power supply and a controller.

It should be understood that any appropriate power supply may be used so long as it is able to provide a desired quantity of electrical energy in order to heat the impression material to within a desired temperature range. As shown in FIG. 21, a preferred system 70 according to the invention includes a dental impression tray 50 as described in FIGS. 17–19, together with a power supply 72 and a controller 74. In one embodiment, the power supply will provide between 5 and 10 volts of DC current at 1.2 amperes to each of heating elements 58a and 58b. The controller 74 may be operated by either the patient or the dental practitioner as desired. Allowing the patient to control the temperature of the dental tray and associated patient dentition within the patient's mouth will allow for optimization between patient comfort and treatment time. The optimum temperature may vary from patient to patient depending on how sensitive a patient is to heat. In general, the optimum temperature in terms of minimizing treatment time, while being sensitive to patient comfort, will be the maximum temperature at which the patient still feels comfortable and is not experiencing excessive pain or discomfort.

In a preferred embodiment, the temperature within the impression material may be measured by means of a diode (not shown), which is an extremely inexpensive device for measuring temperature but which is preferred where impression tray 50 is intended to be disposable. While diodes are not necessarily as accurate as other devices for measuring temperature, such as thermocouples, they have adequate accuracy within the narrow temperature ranges involved in the present invention (e.g., preferably about 110–150° F., more preferably about 120–140° F.).

Figure 15:
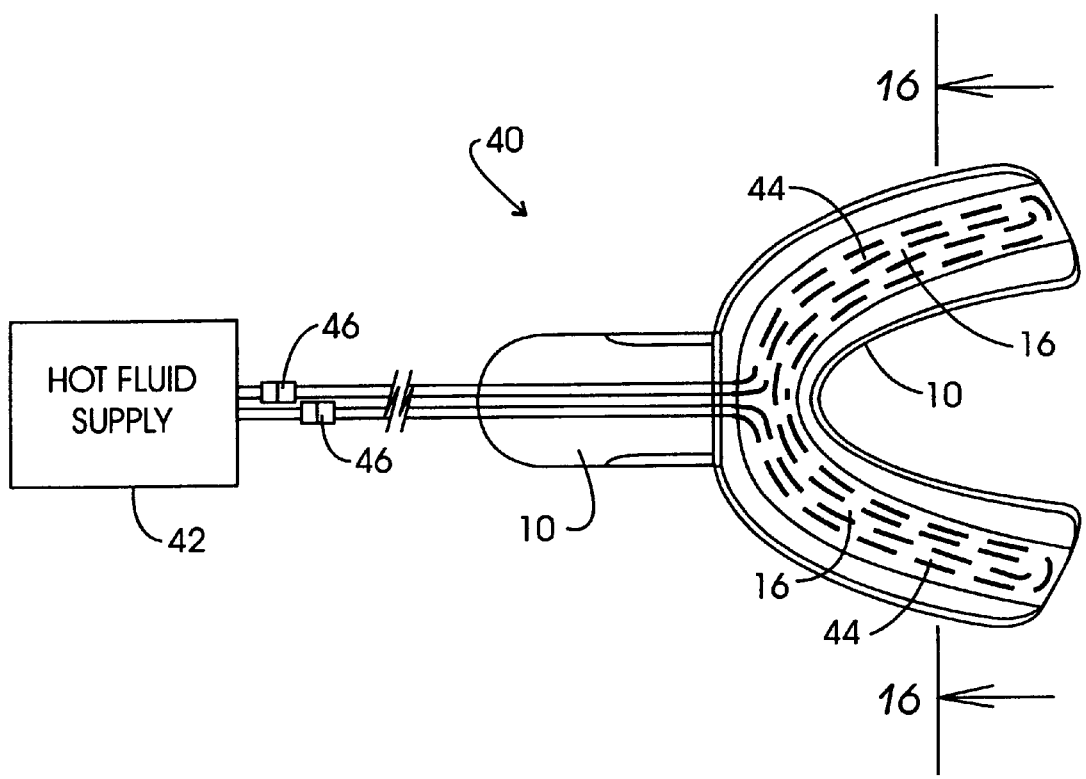
FIG. 15 schematically depicts another alternative embodiment of a dental impression material and impression tray in which a heated fluid is used to heat and maintain the proper temperature of the set dental impression material.
Figure 16:
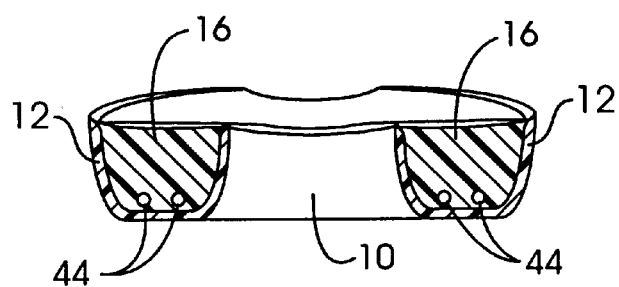
FIG. 16 is a cross-section view taken at line 16-6 of FIG. 15.

FIGS. 15 and 16 depict an alternative system 40 for continuously heating a patient dentition impression tray 10 during a desired dental treatment regimen. System 40 includes a hot fluid supply 42 in fluid communication with a looped tubular fluid conduit 44 disposed within the principal cavity 12 of the impression tray 10. The fluid conduit 44 may be selectively connected to and disconnected from the hot fluid supply 42 by means of conventional fluid connectors 46. In this embodiment, the dental impression tray 10 is provided with the looped fluid conduit 44 disposed in the bottom of principal cavity 12 prior to filling the cavity 12 with unset or uncured dental impression material 16. In an experimental embodiment of apparatus 40, ⅛ inch rigid plastic fluid conduit was used as fluid conduit 44 connected to a supply 42 of water heated to approximately 130° F. Satisfactory results were obtained where the apparatus was retained in a patient's mouth for a period of time in a range of about 5 minutes to about 20 minutes.

The afore-mentioned resistive heating elements or wires and the heated fluid constitute different examples of heating means for heating a formed patient dentition impression. Another example of a resistive heating device is an etched resistive circuit. For purposes of this disclosure and the appended claims, the term "heating means" generally includes any heating apparatus known in the art that is or can be adapted for use with a dental impression tray to heat a formed patient dentition impression. Moreover, the term "fluid" shall be understood to broadly include substances in a gaseous, liquid or supercritical fluid state.

Other dental impression trays may alternatively be used in connection with the present invention, including those illustrated in FIGS. 1–12. FIGS. 1–12 depict one possible method sequence using a conventional dental impression tray 10 that includes a principal cavity 12. Even though FIGS. 1–12 depict a method of using a conventional dental impression tray 10, the general method steps illustrated therein may be generalized as having applicability to methods that employ the dental trays depicted in FIGS. 13–21, keeping in mind that some of the steps depicted in FIGS. 1–12 are merely optional. While certainly within the scope of the invention, the use of a conventional dental impression tray that is not adapted with heat generating means will of typically require the use of an external heat source, such as a heater or microwave capable of temporarily imparting heat energy to the dental tray and/or included patient dentition impression.

III. Methods of Treatment.

In general, any method that employs the use of a heated patient dentition impression in order to accelerate the treatment of a patient's teeth using a dental composition is within the scope of the invention. The term "dentition impression" should be broadly interpreted to include any depression or void space formed within an impression material regardless of whether or not the depression closely or only very roughly approximates the patient's teeth. Preformed, non-custom depressions or void spaces formed within an impression material are within the scope of the term "dentition impression".

It has been found that heating and maintaining dental compositions such as dental bleaching, desensitizing or remineralizing compositions at elevated temperatures using a heated dentition impression greatly reduces the treatment time. In some cases (e.g. in dental bleaching), the heat causes more rapid decomposition of the active ingredient. In other cases (e.g., in desensitizing or remineralizing), the heat does not cause the active ingredient to decompose but nevertheless increases the rate by which the active ingredient interacts with a person's teeth in order for the active ingredient to impart its beneficial properties. The use of a heated dentition impression greatly reduces the time and hassle, and increases patient comfort, compared to treatments that utilize conventional heat sources, such as lasers or dental curing lamps.

In an exemplary method for utilizing the apparatus disclosed herein in order to carry out accelerated treatment of a patient's teeth, the following steps are employed: (1) filling at least a portion of a dental impression tray with a dental impression material, preferably an unset dental impression material; (2) placing the filled dental impression tray into the patient's mouth in order to take an impression of at least a portion of the patient's teeth; (3) maintaining the impression tray in place for a sufficient length of time for the dental impression material to at least partially cure to thereby form a patient dentition impression; (4) removing the dental impression tray and included formed patient dentition impression from the patient's mouth; (5) placing an appropriate quantity of a dental composition within the formed patient dentition impression; (6) introducing the dental impression tray including the formed patient dentition impression and dental composition into the patient's mouth so as to at least approximately register the patient's teeth with the formed patient dentition impression; (7) heating and/or maintaining the temperature of the formed patient dentition impression at a temperature of at least about 105° F. (preferably in a range of about 110° F. to about 150° F., more preferably in a range of about 120° F. to about 140° F.); and (8) removing the dental impression try and included dentition impression from the patient's mouth and thoroughly rinsing the patient's mouth.

Figure 1:
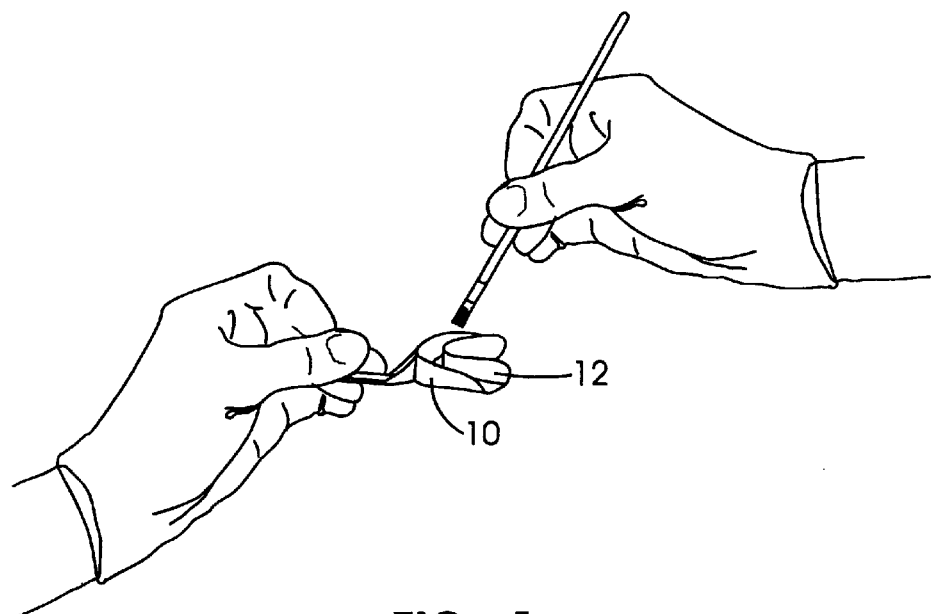
FIG. 1 depicts a preliminary procedural step of coating the principal cavity of an alginate dental impression tray with a conventional adhesive.

In order to illustrate one exemplary method for treating a patient's teeth according to the invention, reference is now made to FIGS. 1–12. FIG. 1 depicts an optional preliminary step of brushing or otherwise applying a dental impression adhesive onto the surface of the principal cavity 12 of a conventional, disposable alginate dental impression tray 10. In one embodiment, one such tray 10 is required for the mandibular (or lower) teeth that are to be whitened, and a separate but like tray 10 may be used for treating the patient's maxillary (or upper) teeth. It will be appreciated, however, that it is within the scope of the invention to utilize a two-sided impression tray capable of receiving impression material sufficient for both the top and bottom teeth.

Figure 2:
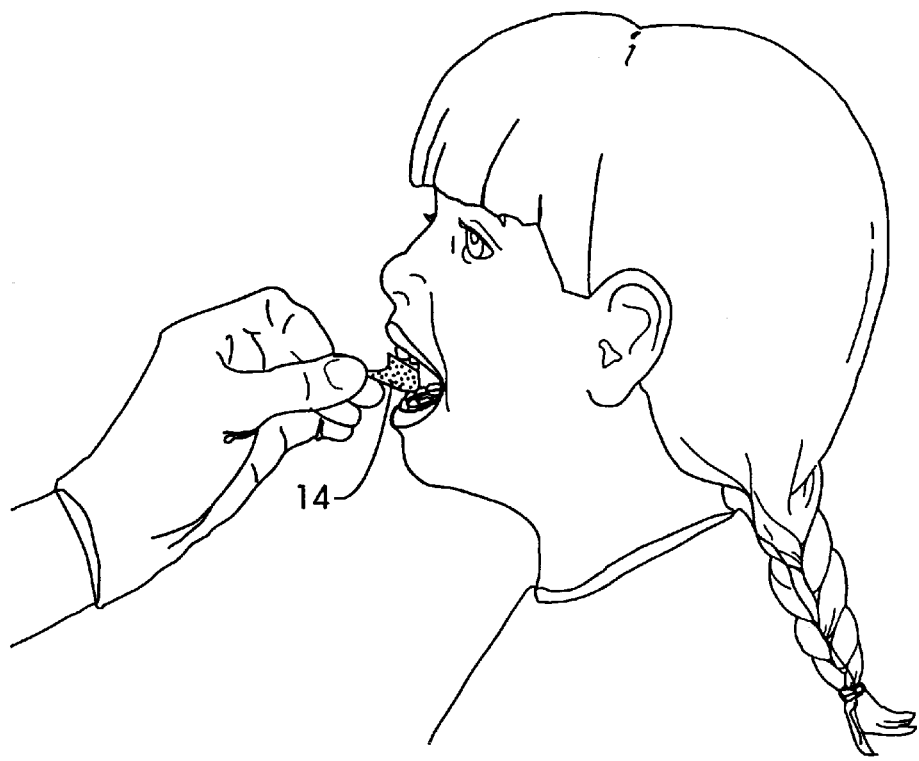
FIG. 2 depicts a preliminary step of applying a dental wax overlay to the surfaces of the patient's teeth that are to be whitened.

FIG. 2 depicts an optional step of applying a sheet-like dental wax overlay 14 onto those surfaces of the patient's teeth that are to be whitened—usually just to the facial aspects of the teeth. The purpose of the wax sheet is to create more space between the formed dental impression and the patient's teeth so as to hold an additional quantity of dental composition, if desired. It should be understood, however, that treatment of the patient's teeth is possible with or without this extra space formed as a result of the wax overlay 14. Other blockout materials may be used, such as curable liquids, coatings or pliable materials, collectively referred to as "amorphous blockout materials".

Figure 3:
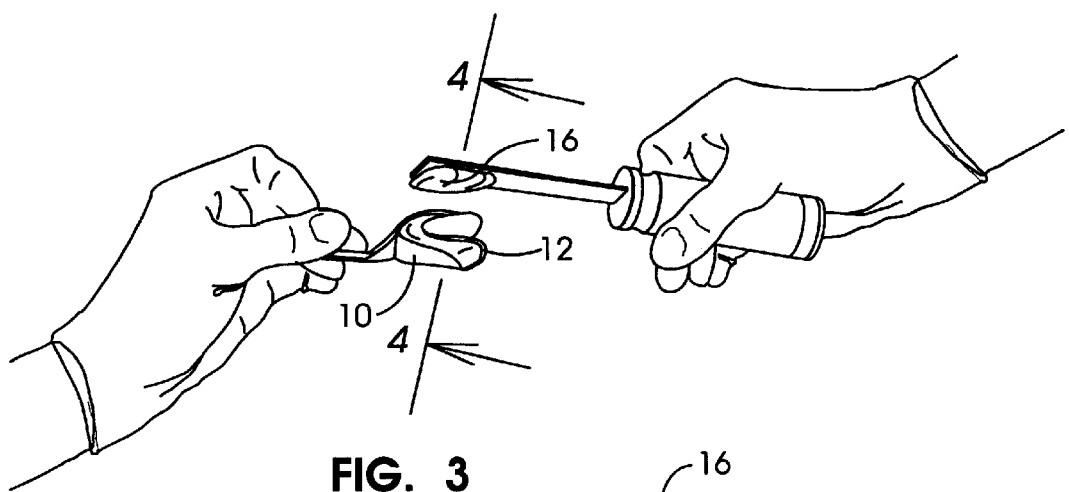
FIG. 3 illustrates the step of placing an unset conventional dental impression material in the principal cavity of the dental impression tray of FIG. 1.
Figure 4:
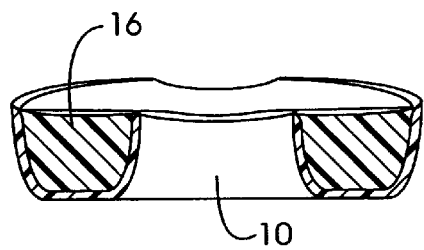
FIG. 4 is a cross-section view taken at line 4—4 of FIG. 3 and extending transversely through the filled dental impression tray of FIG. 3.

FIG. 3 depicts the step of filling the principal cavity 12 of an impression tray 10 with a suitable quantity of an impression material 16, typically an unset alginate dental impression material or catalyzed dental impression compound. FIG. 4 is a cross-sectional view of a tray 10 according to FIG. 3 that has been filled with impression material 16 prior to insertion of the tray 10 into the patient's mouth.

Figure 5:
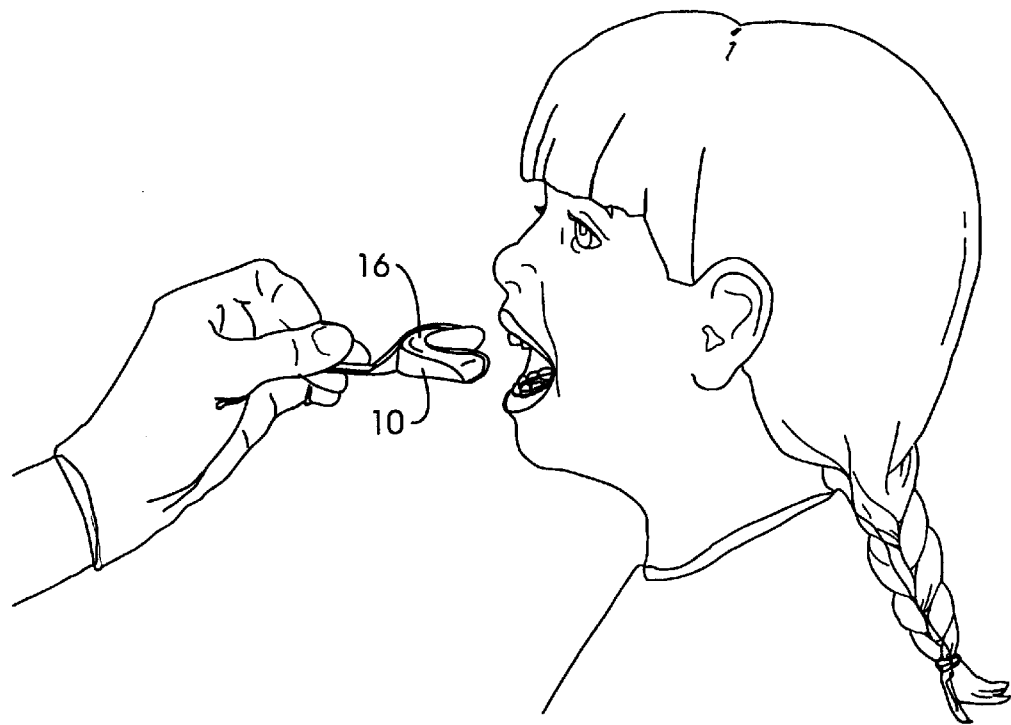
FIG. 5 depicts the act of inserting the compound-filled dental impression tray of FIGS. 3 and 4 into a patient's mouth for impression-setting purposes.

FIG. 5 depicts the step of inserting the impression tray 10 and impression material 16 into a patient's mouth. Thereafter, the patient is asked to gently bite down into the impression material 16 so as to conform the impression material 16 to the shape of the patient's teeth and thereby form a patient dentition impression 18 (see FIG. 6). In a preferred embodiment, the impression material 16 will comprise a curable impression material, and the tray 10 will be held in place within the patient's mouth for a sufficient length of time for the dental impression material 16 to at least partially set or cure in order to yield a formed dentition impression 18 that will maintain its shape when removed from the patient's mouth.

Following removal of dental impression tray 10 with its included formed patient dental impression 18 from within the patient's mouth, any wax overlay or other blockout material 14 that is retained on the surfaces of patient dentition impression 18 is manually removed from the impression 18 by appropriate manual scraping or the like. In addition, some of the impression material defining the dentition impression 18 may be trimmed away in order to reduce or eliminate subsequent contact of the heated impression material with sensitive gingival tissues. FIGS. 6 and 7 depict the set patient dentition impression 18 with wax overlay material 14 in place. FIG. 8 is similar to FIG. 7 but illustrates the formed patient dental impression 18 with the wax overlay material 14 having been removed.

FIGS. 9 and 10 are alternative cross-sectional views of the tray 10 of FIG. 6 depicting the use of different types of impression materials. FIG. 9 depicts a patient dentition impression 18 formed from a conventional impression material, e.g., alginate. FIG. 10 alternatively depicts an impression tray 10 and set patient dentition impression 22 formed from an impression material that includes a particulate filler material. The particulate filler material is included in order to increase the specific heat of the patient dentition impression 22 so that it is capable of absorbing and transferring a greater quantity of heat energy per unit of time.

Figure 11:
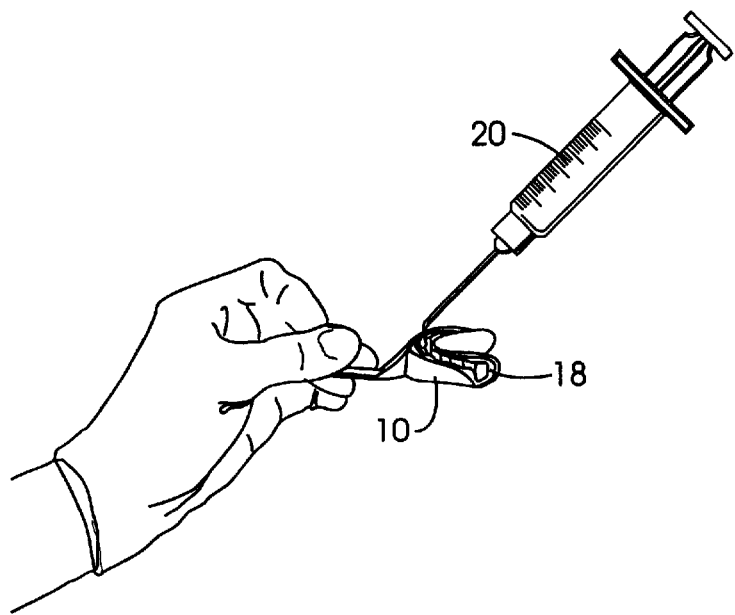
FIG. 11 depicts the step of placing a dental composition into the formed dental impression cavity preparatory to treating the patient's teeth.

FIG. 11 depicts the step of loading the patient dentition impression 18 (or 22) with a dental composition by means of a syringe 20. An example of an appropriate bleaching composition is a 15% carbamide peroxide gel whitener or bleaching agent, optionally or alternatively with a fluoride and/or potassium nitrate additive. Because the act of placing the dental tray 10 into the patient's mouth will typically cause the dental composition to spread out and coat the tooth surfaces, there is no specifically required method of loading the dentition impression 18 (or 22). In one embodiment, it may be desirable to coat the interior labial surfaces of the set patient dentition impression 18 (or 22) corresponding to the patient tooth surfaces to be treated with approximately 0.5 to 1 cc. of the dental composition. The tray is then inserted into the patient's mouth in a manner so as at least approximately register the formed patient dentition impression 18 (or 22) with the patient's teeth to be treated.

Figure 12:
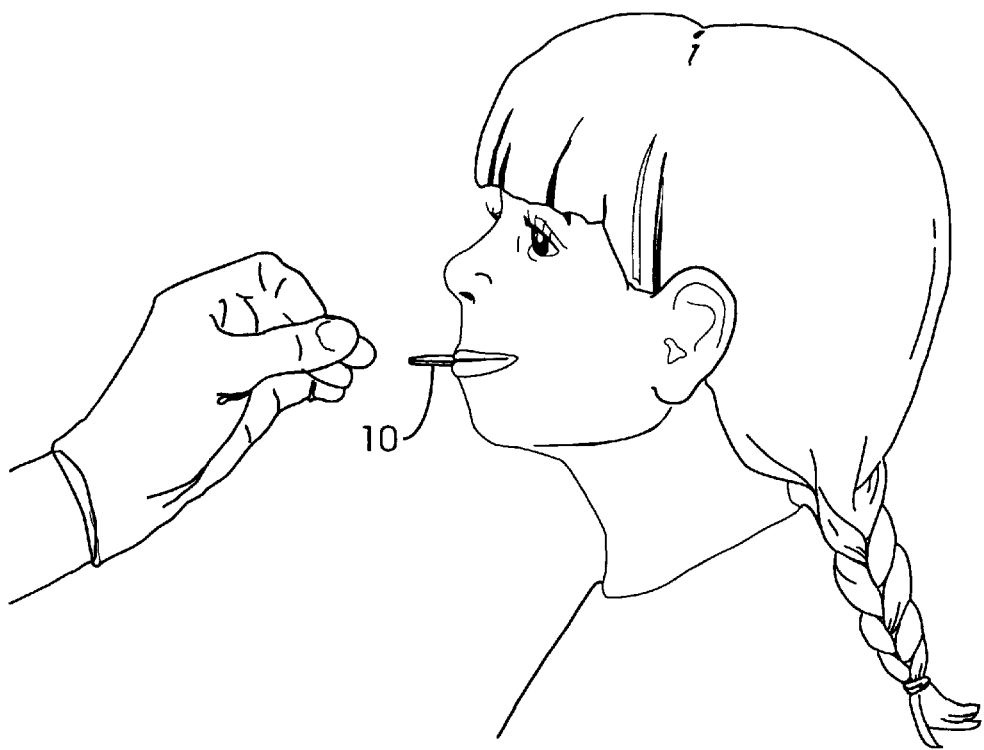
FIG. 12 depicts the placement of the tray of FIG. 11 into the patient's mouth in order to effect bleaching.

FIG. 12 depicts the step of treating the patient's teeth. The tray 10 and set patient dentition impression 18 (or 22) are typically heated before or after insertion of the tray into the patient's mouth, depending on the type of heat source that is employed. In the case where the dental tray includes a heating means, such as a resistive heating element or a heated fluid, the tray is typically heated after insertion into the patient's mouth, although it may optionally be preheated prior to insertion into the patient's mouth. On the other hand, in the case where the tray is heated using a completely external heat source, such as a heater or microwave, the tray will typically be heated before insertion into the patient's mouth, with stored heat providing the desired energy for heating the dental composition.

Regardless of the method used to heat the formed dentition impression, the formed dentition impression and/or the dental composition should be maintained at a temperature of at least about 105° F. in order to accelerate the activity of the active dental agent. The dental composition and/or formed dentition impression are preferably heated and maintained at a temperature in a range of about 110° F. to about 150° F., more preferably in a range of about 120° F. to about 140° F., during treatment.

In addition, the dental tray will typically remain in the patient's mouth for a period of time in a range of about 1 minute to about 60 minutes, more preferably in a range of about 5 minutes to about 30 minutes, depending on the dental treatment being performed, the strength of the active dental agent, the operating temperature(s), and the like. Although not a precise measurement, it has been found that, for every 10 degree increase in the operating temperature, the time period for performing a particular dental treatment is cut approximately in half. In the case where a tray is heated externally, such as by means of microwave energy, it may be necessary to reheat the tray periodically as it cools off in the patient's mouth, optionally with the additional step of replenishing the dental composition.

IV. Compositions Used in Conjunction with the Inventive Apparatus and Methods.

In general there are two different types or classes of compositions that will be used together with the inventive apparatus—an impression material used to form a dentition impression and a dental composition used to carry out a desired dental treatment. The present invention contemplates the use of both conventional impression materials and dental compositions, as well as impression materials and dental compositions that may be specially formulated for use in conjunction with the inventive apparatus.

A. Impression Materials.

Any plastic and deformable material known in the art that is capable of making an impression of a person's teeth may be used in combination with the apparatus of the present invention. In order for the dentition impression to be easily formed and then maintain its shape once formed, it will be preferable to use a material that can set or cure in a relatively short period of time, such as in a matter of minutes or even seconds, after being placed into a patient's mouth.

Alginate impression materials are presently the preferred impression material according to the invention. Alginate impression materials are a common feature in most dental offices and are regularly used to make impressions of a patient's teeth for a variety of reasons. Therefore, dentists are familiar with how alginates are mixed, utilized and set to form a reliable and resilient dentition impression. Alginate materials are also non-toxic and are set or cured by hydration with water. They are relatively inexpensive and readily available. Because they are initially water soluble, a wide range of flavorants may be used to enhance the taste and decrease the tendency of patients to gag while taking an impression.

Notwithstanding the foregoing, virtually any settable impression material may be used. Examples of alternative impression materials include silicone rubbers, polyethers, and epoxies.

In order to increase the heat capacity of dental impression materials, particularly materials such as silicone, polyethers or epoxies that do not absorb or transfer heat as well as alginate materials, it may be desirable to mix a heat-retention material into the impression material, such as a particulate or fibrous filler. Examples of suitable materials that may be used to increase the heat capacity and/or the heat transference properties of the impression materials include metal fibers or powders, ceramic fibers or powders, or mineral fibers or powders.

By way of example, polished 2 mm.–3 mm. size, stone chips may be added and uniformly mixed into an unset alginate dental impression composition in the ratio of approximately 12½ parts by weight of polished dental stone chips to approximately 87½ parts by weight of unset alginate dental impression material. Inclusion of the aggregate in the composition extends the length of time during which the patient dental impression, following heating by microwave oven equipment or other heating means, will remain above the minimum temperature of about 105° F. while being held in the patient's mouth.

On the other hand, the heat transferability qualities of impression materials such as silicone and polyethers, which do not readily transfer heat, may be increased through the use of more conductive fillers such as those based on metals or more conductive ceramics materials.

B. Dental Compositions.

It is within the scope of the invention to utilize any dental composition that may be found to have increased activity or reduced treatment time when subjected to heat. Examples include dental bleaching compositions, desensitizing compositions, and remineralizing compositions. Dental bleaching compositions are characterized by the inclusion of a dental bleaching agent, e.g., carbamide peroxide, aqueous hydrogen peroxide, sodium perborate, and the like. Desensitizing compositions are characterized by the inclusion of a desensitizing agent, e.g., potassium nitrate, other potassium nitrate salts like potassium citrate, citric acid, citric acid salts, strontium chloride, fluoride salts, and the like. Remineralizing compounds are characterized as including a fluoride salt such as sodium fluoride, stannous fluoride, sodium monofluorophosphate, and the like.

It will be readily understood that the dental compositions according to the present invention may include a plurality of active agents, such as two or more of a bleaching agent, a desensitizing agent, a remineralizing agent, or some other active dental agent (whether or not activated by heat so long as the composition includes at least one active agent that is activated by heat).

It is within the scope of the invention to use both conventional bleaching compositions known in the art as well as bleaching compositions that may be specially formulated to take advantage of the heat-induced bleaching activity described herein. In general, dental bleaching compositions that include relatively high concentrations of bleaching agent (e.g., 35%) and are highly stable for good shelf life are well-suited for use in the present invention. Nevertheless, it is certainly within the scope of the invention to use two-part systems that become destabilized upon mixing the parts, or even bleaching compositions having lower concentrations of bleaching agent (e.g., 5–10%).

A wide range of dental bleaching compositions are available from Ultradent Products, Inc., located in South Jordan, Utah, under the general name of Opalecence®. Opalecence® products sold and distributed to patients for in-home use are available in various strengths measured by the concentration of the bleaching agent, which, in the case of presently formulated at-home bleaching compositions, is carbamide peroxide. In particular, Opalecence® formulated for home-use is available in concentrations of 10%, 15% and 20% by weight carbamide peroxide. Opalecence® Quick, which is specially formulated for non-dentist supervised bleaching on site in a dental office waiting area, includes 35% by weight carbamide peroxide. Opalecence® Extra, which is specially formulated for dentist supervised in-office bleaching, contains 35% by weight of hydrogen peroxide together with a light-absorbing component for absorbing light from a radiant energy source, such as a dental curing light or a laser.

Compositions and methods for manufacturing a wide range of dental bleaching compositions, such as those exemplified by Opalecence® brand bleaching compositions, are generally described in U.S. Pat. No. 5,376,006. Compositions and methods for manufacturing a wide range of dental bleaching compositions that include higher concentrations of bleaching agent, are generally described in U.S. Pat. No. 5,858,332. Compositions and methods for manufacturing a wide range of dental bleaching compositions that include a light-absorbing component and optionally higher concentrations of bleaching agent, are generally disclosed in U.S. Pat. No. 5,785,527. For purposes of disclosing dental bleaching compositions suitable for use in conjunction with the apparatus, methods and kits of the present invention, the foregoing patents are incorporated herein by reference.

Ultradent Products, Inc. also sells a desensitizing composition under the name of UltraEZ®, which includes 3% by weight potassium nitrate and 0.11% by weight fluoride ion within a sticky, viscous gel formulation. A duel desensitizing/remineralizing composition that includes 1.1% by weight sodium fluoride is sold under the name of Flor-Opal®. In addition, a variety of blended compositions that include various concentrations of carbamide peroxide (10%, 15% or 20%), together with 3% potassium nitrate and 0.11% fluoride ion, are sold under the name of Opalecence® PF. Finally, blended compositions that include various concentrations of carbamide peroxide (15% or 20%), together with 0.11% fluoride, are available under the name of Opalecence® F.

Compositions and methods for manufacturing a wide range of desensitizing compositions, such as those exemplified by UltraEZ®, or blended bleaching compositions such as Opalecence® PF, are generally described in U.S. Pat. No. 5,855,870 and U.S. Pat. No. 5,851,512. Compositions and methods for manufacturing remineralizing compositions that include a fluoride salt are generally described in U.S. Pat. No. 5,376,006. For purposes of disclosing dental compositions suitable for use in conjunction with the apparatus, methods and kits of the present invention, the foregoing patents are incorporated herein by reference.

V. Kits.

It is within the scope of the invention to sell, or otherwise provide, one or more of the foregoing apparatus and compositions in the form of a kit. For example, a kit may advantageously include a dental impression tray and one or more dental compositions. In a preferred embodiment, a kit may advantageously include a dental impression tray having means for heating a formed patient dentition impression, such as a resistive heating element, and one or more of a dental bleaching composition, a desensitizing composition, a remineralizing composition, or a blended composition that includes more than one active dental agent. The kit may include multiple dental impression trays together with multiple doses of one or more dental compositions. For simplicity of storage and delivery, the dental compositions may advantageously be loaded into and delivered from a syringe, such as a syringe that includes a unit dose of the dental composition.

Although the kit may also include an impression material, this may not be necessary in many cases in view of the fact that many dentists typically keep ample alginate impression material on hand to take dental impressions for a variety of different reasons. Virtually any material capable of taking a dentition impression may be used within the kits of the present invention. Alginate impression materials are presently preferred due to their low cost, ready availability and ease and familiarity of use.

A particulate or fibrous filler for increasing the heat capacity and/or heat transferability may be included within the kits, either alone, in combination with but separate from an impression material, or premixed within an impression material.

The kits may also include a suitable power supply designed to provide a desired amount or range of power in order to heat and maintain the dental impression tray and accompanying impression material at a desired temperature or within a desired temperature range. In the case where the impression trays are disposable, i.e., are to be used and then disposed of after each use, it will generally only be necessary to purchase one power supply (or optionally one power supply per dental chair in the case of multiple-chair offices) that may be used with a series of trays purchased at the same time as the power supply or thereafter.

The kits may include one or more wax overlay sheets in order to act as a blockout material on the surface of the patient's teeth (see FIG. 2). Alternatively, the blockout may be an amorphous material that can be brushed, sprayed or other pressed onto the tooth surfaces. The term "amorphous blockout material" shall broadly include any material other than a sheet that can be applied to a person's teeth in order to temporarily increase the apparent thickness of the teeth during formation of the patient dentition impression. One purpose for doing this is to increase the size of the dentition impression, particularly at the interface between the impression material and the labial tooth surfaces to be treated, in order to create a reservoir for the inclusion of additional dental composition during treatment.

VI. Summary.

The invention provides apparatus and methods for use in accelerating the bleaching activity of conventional bleaching compositions in a manner that is both more comfortable from the point of view of the patient and more economical in terms of cost and time.

The invention further provides apparatus that is disposable and that is of sufficiently low cost and simplicity of design so that it can be used for a single patient and then disposed of.

The invention also provides apparatus and methods that can be used to accelerate the activity of other dental compositions, such as desensitizing and/or remineralizing compounds that include, e.g., a potassium nitrate and/or fluoride salt.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A kit for use in treating a person's teeth comprising:
   a dental impression tray including means for receiving a dental impression material used in making an impression of at least a portion of a person's teeth and means for heating the dental impression material received by said dental impression tray; and
   at least one dental composition suitable for placement within an impression of, and for application to, at least a portion of a person's teeth in order to carry out a desired treatment.

2. A kit as defined in claim 1, wherein said dental impression tray includes a generally arcuate structure defining an interior region configured to receive a dental impression material, a handle attached to said arcuate structure, a resistive heating element disposed at least partially within or adjacent to said interior region, and electrical wires in electrical communication with said resistive heating element for transmitting an electric current to said heating element.

3. A kit as defined in claim 2, wherein said electrical wires are attached to or embedded at least partially within said handle.

4. A kit as defined in claim 2, wherein the resistive heating element includes at least one of a resistive wire, an etched resistive circuit, or a metallic strip.

5. A kit as defined in claim 2, wherein said arcuate structure includes an interior surface oriented so as to be approximately parallel to a person's tooth surfaces when the dental impression tray is positioned within the person's mouth, wherein the impression tray further includes a substantially planar barrier orthogonal to said interior surface of the arcuate structure and oriented so as to receive impression material on at least one surface of said barrier.

6. A kit as defined in claim 5, wherein said barrier bisects the interior region defined by said arcuate structure in a manner so as to create an upper interior region oriented so as to receive impression material for making an impression of at least a portion of a person's upper teeth and a lower interior region oriented so as to receive impression material for making an impression of at least a portion of a person's lower teeth.

7. A kit as defined in claim 2, wherein said arcuate structure has an approximately U-shaped cross section defining an interior cavity for receipt of dental impression material.

8. A kit as defined in claim 1, wherein the dental composition includes a dental bleaching agent in an amount sufficient to effect bleaching of a person's teeth.

9. A kit as defined in claim 8, wherein the dental bleaching agent includes at least one of carbamide peroxide, hydrogen peroxide, or sodium perborate.

10. A kit as defined in claim 1, wherein the dental composition includes a desensitizing agent in an amount sufficient to reduce sensitivity of a person's teeth.

11. A kit as defined in claim 10, wherein the desensitizing agent includes potassium nitrate.

12. A kit as defined in claim 1, wherein the dental composition includes a fluoride salt.

13. A kit as defined in claim 1, wherein the dental composition is stored within a syringe.

14. A kit as defined in claim 1, further including power supply means for providing an electric current to the heating means so as to heat and maintain the dental impression material disposed at least partially within said impression tray at a temperature of at least about 105° F.

15. A kit as defined in claim 14, wherein said power supply means includes a temperature control device operable by a person whose teeth are being treated.

16. A kit as defined in claim 14, wherein said power supply means regulates the temperature of the dental impression material by means of a diode associated with said dental impression tray.

17. A kit as defined in claim 1, further including a curable dental impression material.

18. A kit as defined in claim 17, wherein said curable dental impression material is selected from the group consisting of alginate, silicone, polyether, and epoxy.

19. A kit as defined in claim 17, further including a filler material dispersed, or for dispersion, within said curable dental impression material so as to increase at least one of the heat capacity or heat transference of said dental impression material.

20. A kit as defined in claim 1, further including a blockout material for increasing the size of an impression formed of the person's teeth so as to hold an increased amount of said dental composition within the impression.

21. A kit as defined in claim 20, wherein said blockout material includes at least one of a sheet or an amorphous material.

22. A kit as defined in claim 21, wherein said heating means includes at least one conduit for circulating heated fluid through or adjacent to the dental impression material.

23. A kit for use in treating a person's teeth comprising:
    a dental impression tray including a generally arcuate structure defining an interior region configured to receive a dental impression material, a handle attached to said arcuate structure, a resistive heating element disposed at least partially within or adjacent to said interior region, and electrical wires in electrical communication with said resistive heating element for transmitting an electric current to said heating element; and
    at least one dental composition that includes an active dental agent selected from the group consisting of dental bleaching agents, desensitizing agents, remineralizing agents, and mixtures thereof.

24. A kit for use in treating a person's teeth comprising:
    a dental impression tray including:
        a generally arcuate structure defining an interior region configured to receive a dental impression material;
        a handle attached to said arcuate structure;
        a resistive heating element disposed at least partially within or adjacent to said interior region;
        electrical wires, attached to or embedded at least partially within said handle, in electrical communication with said resistive heating element so as to provide an electric current to said heating element during heating of the dental impression material by the resistive heating element; and
        a substantially planar barrier, substantially orthogonal to an interior surface of said arcuate structure, oriented so as to bisect said interior region defined by said arcuate structure in order to create an upper interior region oriented so as to receive impression material for making an impression of at least a portion of a person's upper teeth and a lower interior region oriented so as to receive impression material for making an impression of at least a portion of a person's lower teeth; and at least one dental composition loaded within a syringe that includes an active dental agent selected from the group consisting of dental bleaching agents, desensitizing agents, remineralizing agents, and mixtures thereof.

* * * * *

UNITED STATES PATENT AND TRADEMARK OFFICE
CERTIFICATE OF CORRECTION

PATENT NO. : 6,368,109 B2
DATED : April 9, 2002
INVENTOR(S) : Sherrill F. Lindquist It is certified that error appears in the above-identified patent and that said Letters Patent is hereby corrected as shown below:

Column 2,
Line 19, after "and (6) suitably" change "trimmiing" to -- trimming --

Column 3,
Line 29, after "and included formed" delete "s"
Line 40, before "and included" change "try" to -- tray --

Column 6,
Line 15, before "trays that" change "inpression" to -- impression --
Line 48, after "switch mechanism" add -- . --

Column 9,
Line 33, before "mouth in order" change "pafient's" to -- patient's --.
Line 50, after "dental impression" change "try" to -- tray --

Column 11,
Line 45, after "In general" add -- . --

Column 13,
Line 9, after "name of" change "Opalecence®" to -- Opalescence® --
Line 10, after "products sold" change "Opalecence®" to -- Opalescence® --
Line 14, after "In particular," change "Opalecence®" to -- Opalescence® --
Line 16, before "Quick," change "Opalecence®" to -- Opalescence® --
Line 19, before "Extra," change "Opalecence®" to -- Opalescence® --
Line 28, after "generally" change "descnbed" to -- described --
Line 49, before "PF" change "Opalecence®" to -- Opalescence® --

UNITED STATES PATENT AND TRADEMARK OFFICE
CERTIFICATE OF CORRECTION

PATENT NO. : 6,368,109 B2
DATED : April 9, 2002
INVENTOR(S) : Sherrill F. Lindquist It is certified that error appears in the above-identified patent and that said Letters Patent is hereby corrected as shown below:

Column 13 cont'd,
Line 57, after "as" change "Opalecence®" to -- Opalescence® --

Signed and Sealed this

Ninth Day of July, 2002

Attest:

Attesting Officer

JAMES E. ROGAN
Director of the United States Patent and Trademark Office